(12) United States Patent
Fernandez

(10) Patent No.: US 7,942,878 B2
(45) Date of Patent: May 17, 2011

(54) TWO MEMBERS CERCLAGE TOOL

(75) Inventor: Alberto Angel Fernandez, Montevideo (UY)

(73) Assignee: Synthes USA, LLC, West Chester, PA (US)

( * ) Notice: Subject to any disclaimer, the term of this patent is extended or adjusted under 35 U.S.C. 154(b) by 583 days.

(21) Appl. No.: 11/194,642

(22) Filed: Aug. 2, 2005

(65) Prior Publication Data

US 2007/0043377 A1 Feb. 22, 2007

(51) Int. Cl.
*A61B 17/58* (2006.01)
(52) U.S. Cl. .................. 606/74; 606/103; 269/3; 269/6; 29/268
(58) Field of Classification Search .................. 606/103, 606/74, 86 R, 144–149, 139; 81/415, 416; 29/268, 278, 261; 369/3, 6
See application file for complete search history.

(56) References Cited

U.S. PATENT DOCUMENTS

| | | | | |
|---|---|---|---|---|
| 1,641,077 | A | * 8/1927 | Fouquet | ........................ 140/121 |
| 2,674,143 | A | * 4/1954 | Peterson | ........................ 81/340 |
| 4,312,337 | A | 1/1982 | Donohue | |
| 4,606,335 | A | 8/1986 | Wedeen | |
| 5,071,428 | A | * 12/1991 | Chin et al. | ..................... 606/184 |
| 5,354,301 | A | * 10/1994 | Castellano | ..................... 606/103 |
| 5,501,688 | A | 3/1996 | Whiteside et al. | |
| 5,772,663 | A | 6/1998 | Whiteside et al. | |
| 5,810,832 | A | 9/1998 | Blasingame et al. | |
| 5,851,209 | A | 12/1998 | Kummer et al. | |
| 5,904,078 | A | * 5/1999 | Gustafson et al. | .............. 81/417 |
| 6,086,596 | A | * 7/2000 | Durham | ........................ 606/103 |
| 6,616,667 | B1 | * 9/2003 | Steiger et al. | ..................... 606/61 |
| 2006/0293691 | A1 | * 12/2006 | Mitra et al. | ..................... 606/103 |
| 2009/0306668 | A1 | * 12/2009 | Dell'Oca | ........................ 606/74 |

FOREIGN PATENT DOCUMENTS

GB 2214814 A * 9/1989

* cited by examiner

*Primary Examiner* — Eduardo C Robert
*Assistant Examiner* — Jan Christopher Merene
(74) *Attorney, Agent, or Firm* — Fay Kaplun & Marcin, LLP

(57) ABSTRACT

A cerclage tool for placement of a wire around a bone for internal fixation of the bone comprising a first member having a handle portion, a central portion and a first bent tube portion and a second member having a handle portion, a central portion and a second bent tube portion. The first member and the second member are configured and adapted to be inserted separately through an incision into soft tissue surrounding the bone and subsequently joined together after insertion such that the first bent tube portion and the second bent tube portion form a continuous tube that encircles the bone.

13 Claims, 6 Drawing Sheets

TWO MEMBERS CERCLAGE TOOL

BACKGROUND OF THE INVENTION

The present invention is directed to a cerclage tool, and in particular to an instrument used to position a cerclage wire around a bone for fixation of a fracture such that when the instrument is inserted into the patient, the disruption of surrounding muscle tissue is minimized.

The use of cerclage wires for internal fixation of bone fractures is a well-known technique. Cerclage wiring techniques are frequently used following reduction for provisional fixation of long bone fractures to stabilize the bone for placement of screws, nails or rods, after which the wires are removed. They may also be used for definitive bone fixation, either alone or in combination with other fixation devices.

Cerclage wires are passed around the bone using a wire passer or cerclage tool, so as to lie as perpendicular to the long axis of the bone as possible. Typically, a wire passer or cerclage tool is an instrument having a shaft with a curved end and an eyelet or notch in the curved end for guiding the wire around the bone. These wire passers are available in different curvature diameters and can therefore be used with larger or smaller diameter bones.

Surgical procedures on and in the vicinity of a bone with closely neighboring nerves, arteries, muscle, ligaments, complicated anatomical structures, and other delicate areas represent a difficult and time consuming task for a surgeon.

The difficulty with these procedures is that they need to be performed accurately, minimizing stress, trauma, risk, and injury to a patient, and with as little difficulty for a surgeon performing such procedures, in as rapid a time frame as possible.

The orthopedic procedure is as follows: the curved end of the instrument is positioned around the bone and a wire is inserted into the eyelet so that it can be pulled around the bone as the instrument is withdrawn. After the wire has encircled the bone, the ends are twisted using wire tighteners.

Different surgical tools are known in the art. However, none of the tools adequately satisfies these aforementioned needs. Different instruments have been devised to pass the wire around a bone. Most of the surgical tools known in the art have a handle structure with either a "C" or "S" shaped portion. Some of these instruments, such as that disclosed in U.S. Pat. No. 5,772,663 include a hollow or grooved part for guiding the orthopedic wire therethrough after the instrument is accurately positioned around the bone. As described in U.S. Pat. Nos. 4,606,335 and 5,501,668, other instruments include an eyelet opening at the free end of the curve through which the wire is threaded during the cerclage procedure.

Most of the cerclage devices in the prior art are designed with a curvature to partially encircle the bone shaft and are formed from rigid materials. At certain points in their travel around the bone, these cerclage devices can create a lever action which causes pulling of the soft tissue away from the bone and/or significant spreading of the incision.

For example, U.S. Pat. Nos. 4,606,335, 5,772,663 and 5,501,688 require a significant spreading of an incision in order to allow the tip of the device to completely travel around the bone for insertion of the wire into the eyelet, thus causing trauma to the muscle.

The cerclage wire passer disclosed in the U.S. Pat. Nos. 5,810,832 and 5,851,209 provides a flexible, retractable tip that curves around and adapts to the bone circumference, apparently solving the problem of significant spreading of the incision and muscle trauma. However, these devices have insufficient strength to go through the bone surrounding muscles.

U.S. Pat. No. 4,312,337 shows a scissor-like apparatus that claims to minimize the amount of soft tissue that has to be separated from bone to insert a cerclage wire. However, this device does not position the wire around the bone, but instead, through the bone cortex. It does not perform the same function as that of the present invention and still results in too much tissue and muscle trauma The effectiveness of the cerclage wire has proven itself, but the cerclage procedure itself has proved difficult in many cases. The heretofore instruments fail to provide an adequate technique for positioning a cerclage wire around a bone and may lengthen the overall procedure significantly.

To overcome the foregoing deficiencies of these devices, a new cerclage wire passer is needed that takes into consideration the fact that the wire must be passed around the bone in a simple and reliable manner, without spreading the incision or requiring a large incision to provide the range of movement necessary to guide a rigid trip around the bone without excessive intrusion, exposure or stripping of the bone-surrounding musculature. In addition, a new cerclage wire passer is needed that allows a surgeon to more quickly perform such procedures.

BRIEF SUMMARY OF THE INVENTION

Accordingly, it is an object of the embodiments of the present invention to provide a simple and effective device and method for passing a wire or cable around a bone without requiring a large incision in a patient, while also providing a range of movement necessary to guide the device around the bone by conforming to a circumference thereof.

Another object of the embodiments of the present invention is to provide a device and method wherein the exposure or stripping of the musculature away from the bone is minimized.

One embodiment of the present invention comprises two members, each member having a handle, a central part and a J-shaped tube. When the central parts of both members are firmly coupled together, the J-shaped tubes form a continuous tube through which a wire, cable, band or suture can be fed.

Other objects, advantages and novel features of the present invention will become apparent from the following detailed description of the invention when considered in conjunction with the accompanying drawings.

BRIEF DESCRIPTION OF THE SEVERAL VIEWS OF THE DRAWINGS

Features of the present invention are disclosed in the accompanying drawings, wherein similar reference characters denote similar elements throughout the several views, and wherein.

DETAILED DESCRIPTION OF THE INVENTION

Hereinafter, a method of cerclage wiring according to embodiments of the present invention will be explained with reference to FIGS. 1-6.

Figure 1:
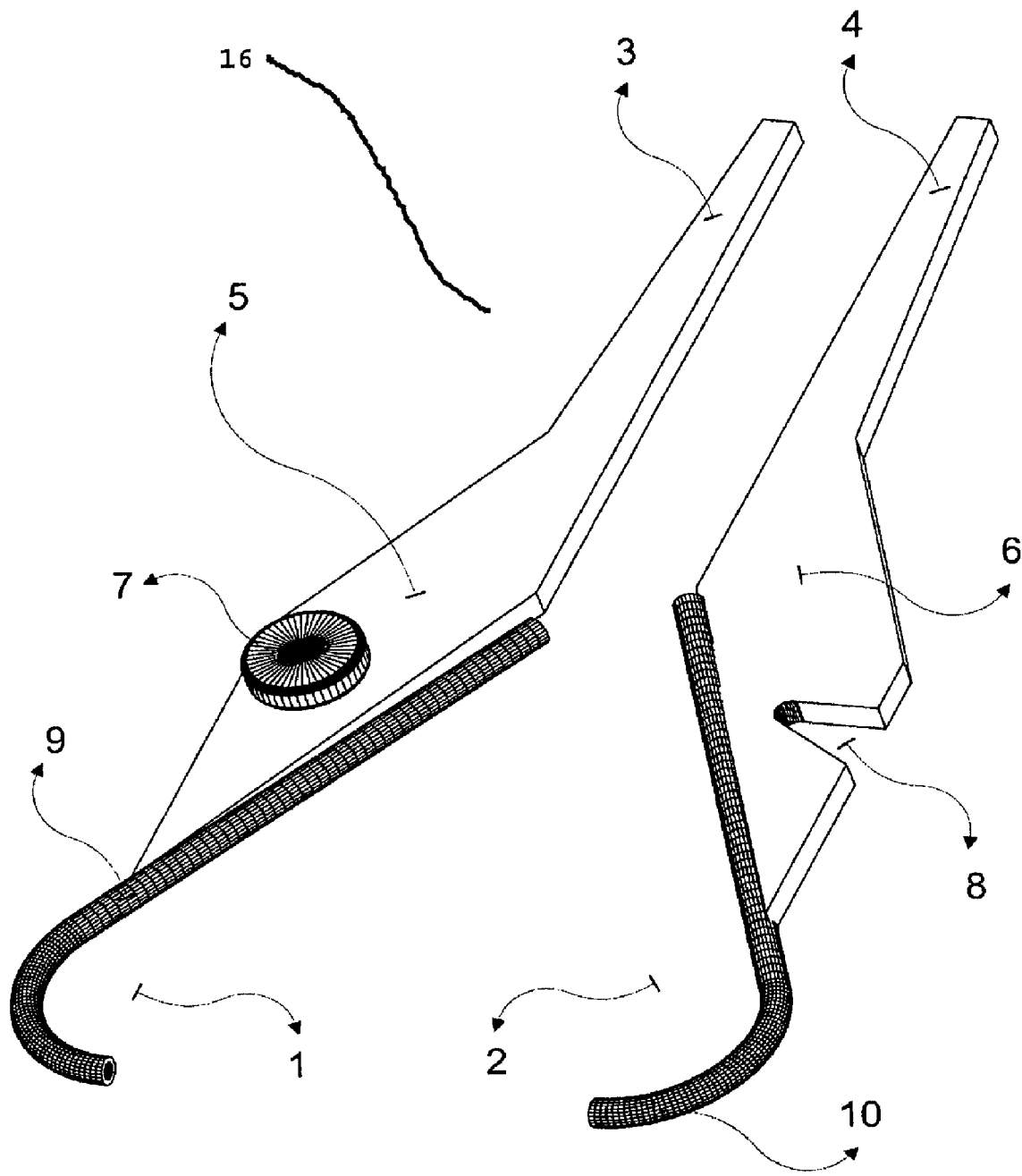
FIG. 1 is a perspective view of a bone cerclage tool, wherein the two separate members are not coupled, according to an exemplary embodiment of the present invention.

FIG. 1 shows a bone cerclage tool or wire/cable passer according to an embodiment of the present invention, designated generally by the reference number 16. The wire/cable passer 16 has two members 1,2. Each member includes: a handle 3,4 to grip the tool and to firmly couple both members 1,2 when both handles 3,4 are pulled close; a central part 5,6; and a J shaped tube 9,10. One of the members 1 of the bone cerclage tool 16, includes a button 7 on its central part 5, while the other member 2 includes a notch 8 in its central part 6.

Figure 2:
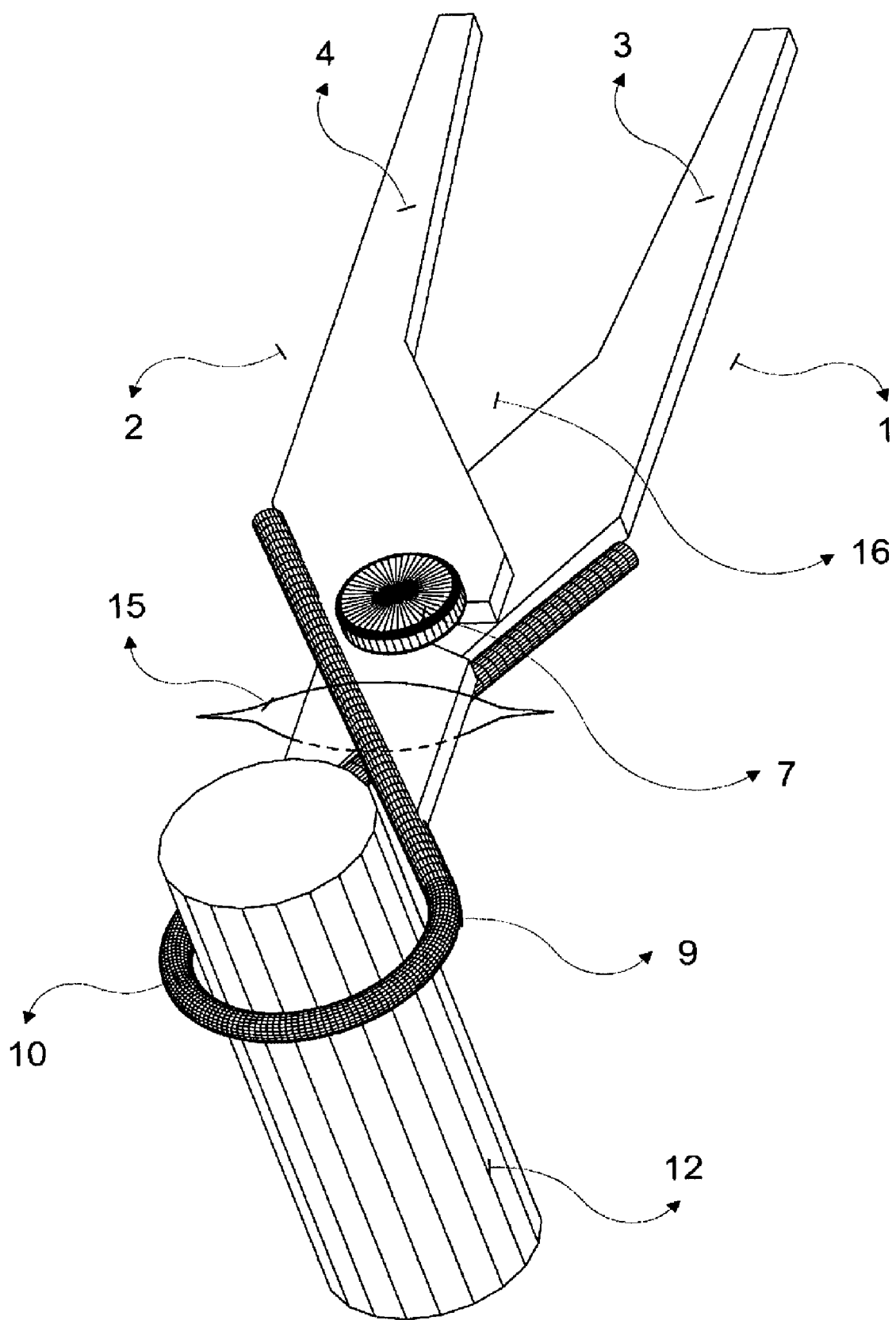
FIG. 2 is a second perspective view of the bone cerclage tool of FIG. 1 wherein the two members are firmly coupled together.

As shown in FIG. 2, after both members 1,2 are coupled together, J shaped tubes 9,10 form a continuous tube around a bone through which a wire cable, band or suture can be fed.

A surgical procedure according to the present invention is described with reference to FIGS. 3-6.

Figure 3:
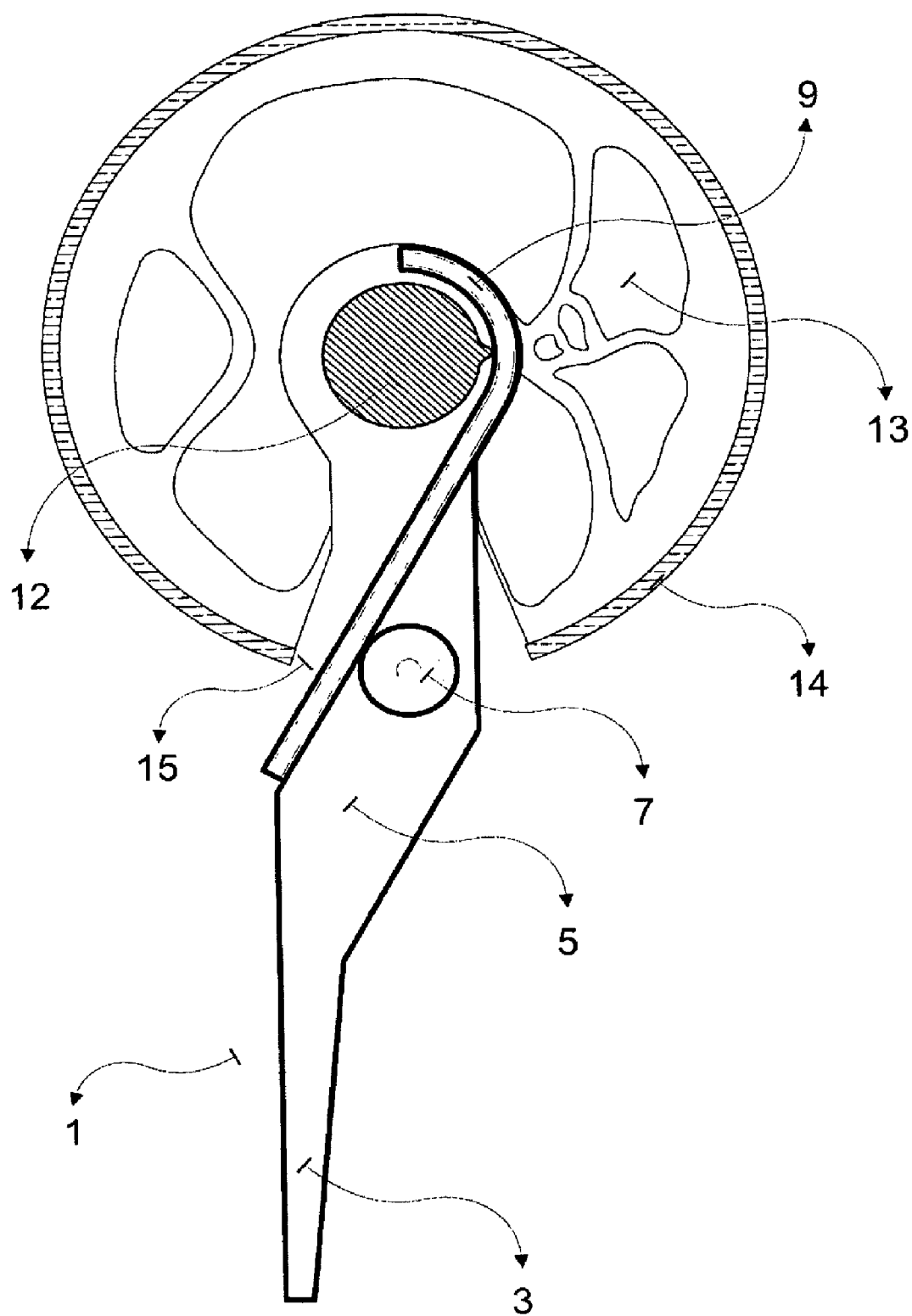
FIG. 3 is a front view of one isolated member of the bone cerclage tool of FIG. 1 inserted around a bone.
Figure 4:
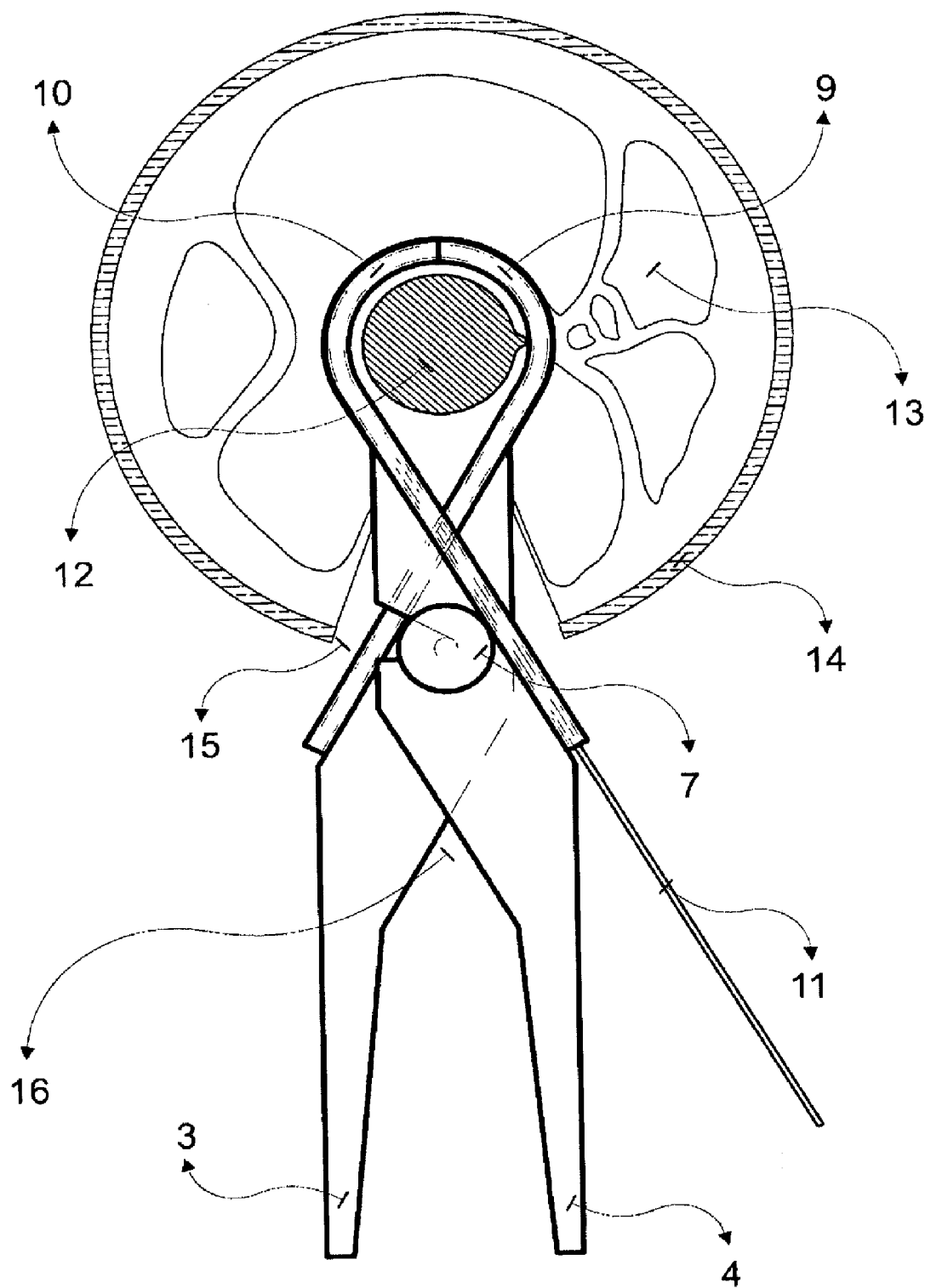
FIG. 4 is a front view of the bone cerclage tool of FIG. 3 inserted about a bone, wherein the two parts are coupled together, and wherein a wire has been fed through the tube.

As shown in FIGS. 3-4, during surgical procedures, each member 1,2 of the bone cerclage tool 16 is independently inserted close to the bone 12 through a small skin incision 15, minimally disturbing skin 14 and muscle 13.

FIG. 4 illustrates the bone cerclage tool 16 in its closed or joined position. After both tool members 1,2 are inserted, they are firmly coupled together by pulling both handles 3,4 close together. The wire 11 can then be fed through the continuous tube formed by the two J-shaped tubes 9,10, which now surround the bone 12.

Figure 5:
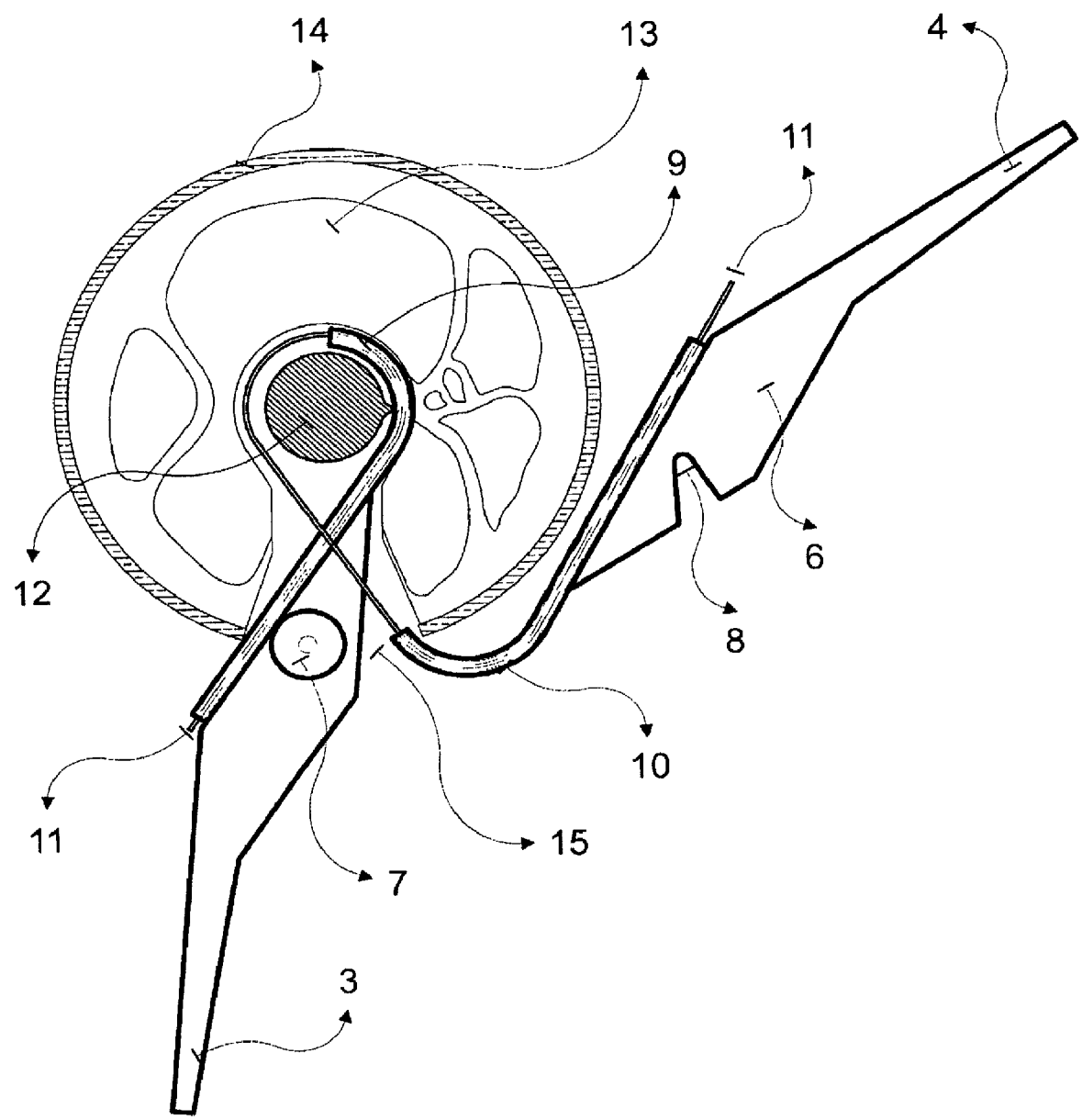
FIG. 5 is a front view of the bone cerclage tool of FIG. 3 in a partially disassembled configuration.

FIG. 5 shows the cerclage tool 16 partially disassembled for removal, wherein only a small incision 15 formed at skin level is required.

Figure 6:
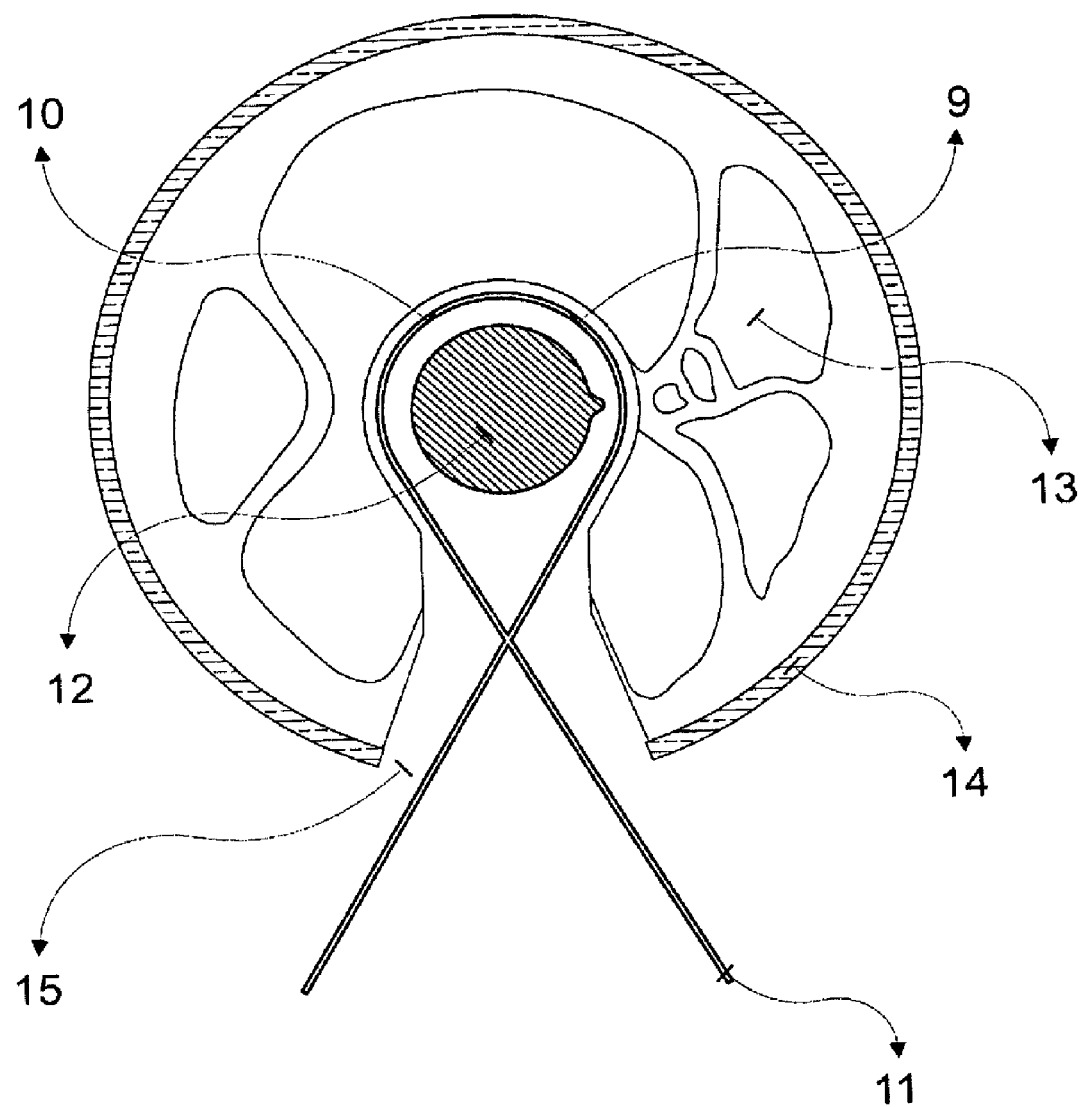
FIG. 6 is a front view of the wire of FIG. 4 looping the bone after the removal of the bone cerclage tool.

The completed surgical procedure is shown in FIG. 6, wherein the wire 11 is left looping the bone 12, after the bone cerclage tool 16 is removed from the patient.

While embodiments of the present invention have been illustrated and described above, it will be understood that those skilled in the art will thereby be enabled to devise variations and modifications without departing from the spirit and scope of the embodiments of the present invention, as defined in the appended claims.

What I claim as my invention is:

1. A cerclage tool for placement of a wire around a bone for internal fixation of the bone, comprising:
    a first member extending from a first proximal end comprising a first handle portion and along a first central portion to a first distal end comprising a first bent tube portion; and
    a second member extending from a second proximal end comprising a second handle portion and along a second central portion to a second distal end comprising a second bent tube portion,
        wherein the first member and the second member are configured and adapted to be inserted individually through an incision into soft tissue surrounding the bone and subsequently joined together after insertion such that the first bent tube portion and the second bent tube portion form a continuous tube with a size and shape formed to encircle the bone, wherein when the first member and the second member are joined together and form the continuous tube, the first bent tube portion and the second bent tube portion crossing over one another to form an angle at a location that is proximal of the bone when viewed from a direction extending perpendicularly into a plane comprising the first and second members, wherein the angle is a non-zero angle.

2. The cerclage tool of claim 1, wherein the first member further comprises a button.

3. The cerclage tool of claim 1, wherein the second member further comprises a notch.

4. The cerclage tool of claim 2, wherein the button is located in the first central portion.

5. The cerclage tool of claim 3, wherein the notch is located in the second central portion.

6. The cerclage tool of claim 1, wherein the first bent tube portion and the second bent tube portion are J-shaped.

7. A device for placing a wire internally around a bone, comprising:
    a first independent member extending from a first proximal end comprising a first handle portion and along a first central portion to a first distal end comprising a first bent tube portion; and
    a second independent member extending from a second proximal end comprising a second handle portion and along a second central portion to a second distal end comprising a second bent tube portion,
    wherein the first independent member and the second independent member are sized and shaped to encircle a bone with the first distal end and the second distal end joined to one another, and wherein when the first independent member and the second independent member are joined together and form a continuous tube, the first bent tube portion and the second bent tube portion cross over one another to form an angle at a location proximal of the bone when viewed from a direction extending perpendicularly into a plane comprising the first and second members, wherein the angle is a non-zero angle.

8. The device of claim 7, wherein the first bent tube portion and the second bent tube portion form a continuous tube that encircles the bone after the first independent member and the second independent member are joined together.

9. The device of claim 6, wherein the first bent tube portion and the second bent tube portion are J-shaped.

10. The device of claim 7, wherein the first independent member further comprises a button.

11. The device of claim 7, wherein the second independent member further comprises a notch.

12. The device of claim 10, wherein the button is located in the first central portion.

13. The device of claim 11, wherein the notch is located in the second central portion.

* * * * *